US011725508B2

(12) United States Patent
Li et al.

(10) Patent No.: US 11,725,508 B2
(45) Date of Patent: Aug. 15, 2023

(54) CRUDE OIL PARAMETER DETECTION DEVICE

(71) Applicant: Shandong Tiangong Petroleum Equipment Co., Ltd., Jining (CN)

(72) Inventors: Xinhua Li, Jining (CN); Haifeng Tian, Jining (CN); Jianlin Wang, Jining (CN); Hailin Kong, Jining (CN); Dedong Kong, Jining (CN); Guohua Xu, Jining (CN)

(73) Assignee: Shandong Tiangong Petroleum Equipment Co., Ltd., Jining (CN)

( * ) Notice: Subject to any disclaimer, the term of this patent is extended or adjusted under 35 U.S.C. 154(b) by 0 days.

(21) Appl. No.: 17/694,195

(22) Filed: Mar. 14, 2022

(65) Prior Publication Data

US 2023/0003122 A1 Jan. 5, 2023

(30) Foreign Application Priority Data

Jul. 2, 2021 (CN) .......................... 202110749854.X

(51) Int. Cl.
*E21B 49/08* (2006.01)
*G01N 33/28* (2006.01)
*G01F 1/22* (2006.01)

(52) U.S. Cl.
CPC ........ *E21B 49/084* (2013.01); *E21B 49/0875* (2020.05); *G01F 1/22* (2013.01); *G01N 33/2823* (2013.01); *G01N 33/2847* (2013.01)

(58) Field of Classification Search
CPC .............. E21B 49/084; E21B 48/0875; G01M 33/2847; G01M 33/2823; G01F 1/22
See application file for complete search history.

(56) References Cited

U.S. PATENT DOCUMENTS

| 2,388,672 A | * | 11/1945 | Brewer | ..................... G01F 1/22 |
| | | | | 73/861.55 |
| 2,400,108 A | * | 5/1946 | Elowson | ................... G01F 1/22 |
| | | | | 137/512.1 |

(Continued)

*Primary Examiner* — Kristina M Deherrera
*Assistant Examiner* — Jean F Morello
(74) *Attorney, Agent, or Firm* — Hamre, Schumann, Mueller & Larson, P.C.

(57) ABSTRACT

The present disclosure relates to a crude oil parameter detection device, which includes a liquid cavity constituted by a first housing, a flow measurement cavity constituted by a second housing, a detection cavity constituted by a third housing, and a processing module; the flow measurement cavity is in-built in the liquid cavity; the first housing includes a first liquid inlet and a first liquid outlet; the second housing includes a second liquid inlet and a second liquid outlet; the second liquid outlet is in communication with the first liquid outlet through a liquid outlet pipeline; a float assembly is in-built in the flow measurement cavity, which includes a float and a float connection rod integrally connected with the float, and an end of the float connection rod is connected to a detection part; the detection cavity at least internally comprises a position detection module; the position detection module detects a position of the detection part at the end of the float connection rod to obtain a float height detection signal; and the processing module calculates a flow rate of measured crude oil according to the float height detection signal. The present disclosure can safely meter the crude oil flow rate of a crude oil transport pipeline and meet the accuracy of metering the crude oil.

16 Claims, 8 Drawing Sheets

(56) References Cited

U.S. PATENT DOCUMENTS 3,024,654 A * 3/1962 Head .................. G01F 1/22
  73/861.57
3,182,500 A * 5/1965 Ishii .................. G01F 1/26
  73/861.57

* cited by examiner

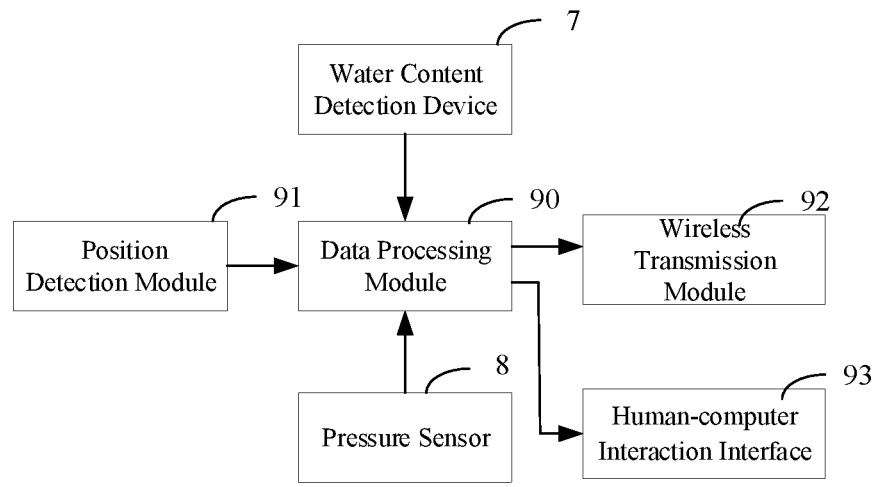
FIG.6
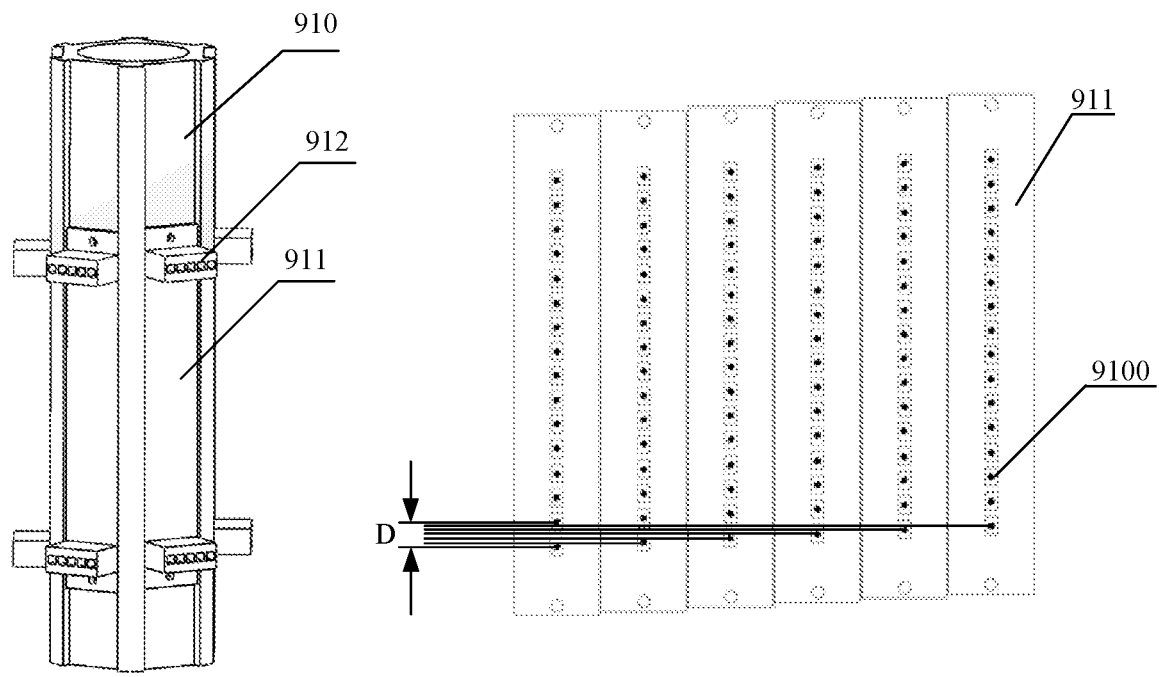
FIG.7
FIG.8

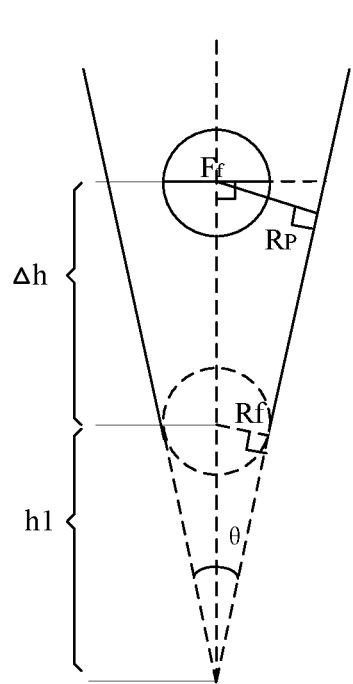 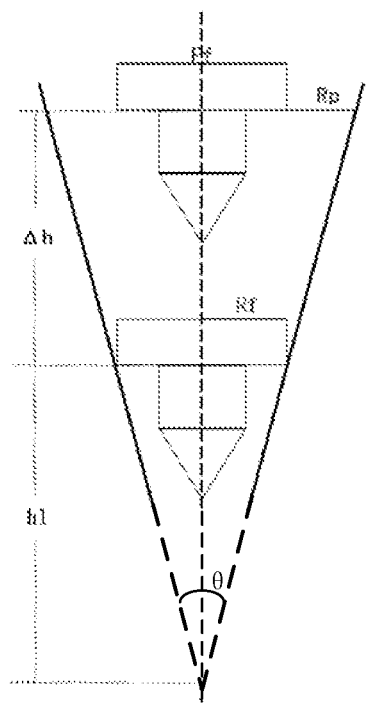
FIG.9     FIG.10
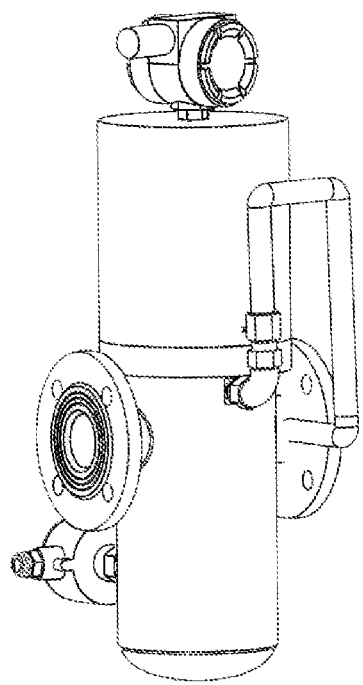
FIG.11

CRUDE OIL PARAMETER DETECTION DEVICE

FIELD OF THE INVENTION

The present disclosure relates to a detection device in the petroleum field, in particular to a crude oil parameter detection device.

BACKGROUND OF THE INVENTION

In the process of oil production, a ground oil extraction apparatus, such as an oil pumping unit, extracts a mixed liquid (hereinafter referred to as crude oil) of oil, gas and water from the formation, which is then transported through a ground pipeline to crude oil processing plants for processing or transported to oil storage tanks for temporarily storage. In order to know about the yield of oil wells, it is necessary to use relevant equipment to meter the yield of oil wells. In theory, flowmeters such as vortex flowmeters, ultrasonic flowmeters, and metal float flowmeters can be installed in the oil transport pipeline to measure the flow rate of crude oil, and then the yield of the oil wells can be obtained through conversion. However, in practical applications, flowing characteristics of the crude oil in the ground pipeline of oil wells are closely related to the way the liquid comes out of the oil wells. The working process of the oil extraction apparatus includes two strokes, i.e., an upward stroke and a downward stroke. During the upward stroke, the crude oil flows out to the ground pipeline through a sucker rod. During the downward stroke, there is basically no crude oil flowing out, so the liquid in the ground pipeline of the oil well will flow stream by stream. In addition, the unprocessed crude oil itself that has just been mined has a complex composition. It is a mixed liquid that integrates oil, gas, water, various other liquid components, and solid particles, which is viscous and has poor fluidity. The liquid will also entrain agglomerated oil mass. If devices such as the above-mentioned vortex flowmeter, ultrasonic flowmeter, turbine flowmeter, and metal float flowmeter are used to measure the flow rate in the ground pipeline of the oil well, first, due to the unique way of discharging liquid of the oil well, the metering error will be too large and the accuracy requirements cannot be met. In addition, due to the liquid properties of the crude oil, a measuring tube of the flowmeter will be easily blocked, which not only makes it impossible to measure, but also easily causes the pressure in the pipeline to rise and burst the pipeline, thereby leading to safety accidents such as oil leakage and pipeline burst. Therefore, there is an urgent need for a flow metering device that is safe, convenient to install, and meets the accuracy requirements. In addition, in order to obtain other parameters of the oil pipeline, such as pipeline pressure and water content of the crude oil in the pipeline, the current common practice is to drill holes in the oil transport pipeline to install these parameter detection devices. The installation positions are arbitrary, and the type of data obtained is single.

SUMMARY OF THE INVENTION

In view of the technical problem existing in the prior art, the present disclosure proposes a crude oil parameter detection device, which can safely meter the crude oil flow rate of a crude oil transport pipeline and meet the accuracy of metering the crude oil.

In order to solve the above technical problem, the present disclosure provides a crude oil parameter detection device, which includes a liquid cavity, a flow measurement cavity, a float assembly, a detection cavity, a connector, a position detection module, and a processing module; in which the liquid cavity is constituted by a first housing, and includes a first liquid inlet and a first liquid outlet; the flow measurement cavity is constituted by a second housing and is in-built in the liquid cavity, and includes a second liquid inlet and a second liquid outlet; the second liquid outlet is in communication with the first liquid outlet through a liquid outlet pipeline; the float assembly is in-built in the flow measurement cavity, and includes a float and a float connection rod integrally connected with the float; an end of the float connection rod is connected to a detection part; the detection cavity is composed of a third housing, and at least internally includes the position detection module; an upper part of the connector is fixed to the third housing constituting the detection cavity, and a lower part of the connector is connected to the first housing constituting the liquid cavity and the second housing constituting the flow measurement cavity respectively; the connector is provided with a through hole, and the end of the float connection rod can protrude out of the detection cavity via the through hole; the processing module is at least connected to the position detection module; when the detection part at the end of the float connection rod extends into the detection cavity, the position detection module detects a position of the detection part at the end of the float connection rod to obtain a float height detection signal; and the processing module calculates a flow rate of measured crude oil according to the float height detection signal.

Preferably, the crude oil parameter detection device further includes: a gas separation structure, which includes a gas separation baffle in-built in the liquid cavity and placed between the second housing and the first housing with a plurality of ventilation holes distributed thereon; a gas inlet provided on the first housing between the gas separation baffle and a lower surface of the connector; a gas outlet provided on the liquid outlet pipeline located outside the liquid cavity; and a gas pipeline, two ends of which are connected to the gas inlet and the gas outlet through interfaces respectively.

Preferably, the crude oil parameter detection device further includes a pressure sensor which is configured to be installed on the upper part of the connector; a pressure sensing part of the pressure sensor communicates into the liquid cavity through the connector, and a signal end of the pressure sensor is connected to the processing module; and the processing module calculates a current pipeline pressure according to a pressure sensing signal sent by the pressure sensor, or receives pressure value data sent by the pressure sensor.

Preferably, the crude oil parameter detection device further includes a water content detection device; a connection base of the water content detection device is installed in the first housing constituting the liquid cavity, a water content sensing end of the water content detection device is in-built in the liquid cavity, and a signal end of the water content detection device is connected to the processing module; the processing module calculates a current water content according to a water content sensing signal sent by the water content detection device, or receives water content data sent by the water content detection device.

During the flow of the measured crude oil from the liquid inlet to the liquid outlet of the measuring tube, the float in the present disclosure can overcome the resistance generated by the viscosity of the crude oil and, in accordance with the flowing pattern (i.e., the crude oil flows stream by stream), rises, stabilizes at a certain height, falls, rises again, stabilizes at a certain height, and falls again, etc. The float can also stabilize at different heights according to the magnitude of the flow rate when the crude oil flows continuously. Therefore, the crude oil parameter detection device provided by the present disclosure can be well adapted to the flowing characteristics of the crude oil and the liquid properties of the crude oil. In addition, transmission mechanisms in the traditional float flowmeters are not used in the present disclosure, so the present disclosure is not subjected to the fatigue damage of the traditional float detection assembly, and the reliability and accuracy of the device for long-term metering can be ensured. In addition, the parameter detection device provided by the present disclosure has a small volume, occupies a small space, is convenient for installation and daily maintenance, and can be integrated with other parameter detection devices in view of actual application requirements, so that multiple types of data can be detected. The device has a strong and durable structure, can be applied to various field environments and work stably for a long time.

BRIEF DESCRIPTION OF THE DRAWINGS

Hereinafter, preferred embodiments of the present disclosure will be described in further detail with reference to the accompanying drawings, in which:

FIG. 6 is a block diagram showing the principle of a control device of a crude oil parameter detection device according to an embodiment of the present disclosure;

FIG. 7 is a schematic structural view of a position detection module according to an embodiment of the present disclosure;

FIG. 8 is a schematic view of six Hall sensor arrays in FIG. 6 after being expanded;

FIG. 9 is a schematic diagram of the calculation principle of a crude oil parameter detection device according to an embodiment of the present disclosure;

FIG. 10 is a schematic diagram of the calculation principle of a crude oil parameter detection device according to another embodiment of the present disclosure;

FIG. 11 is a schematic view of an external appearance of a crude oil parameter detection device according to another embodiment of the present disclosure;

DETAILED DESCRIPTION OF THE EMBODIMENT(S) OF THE INVENTION

Figure 1:
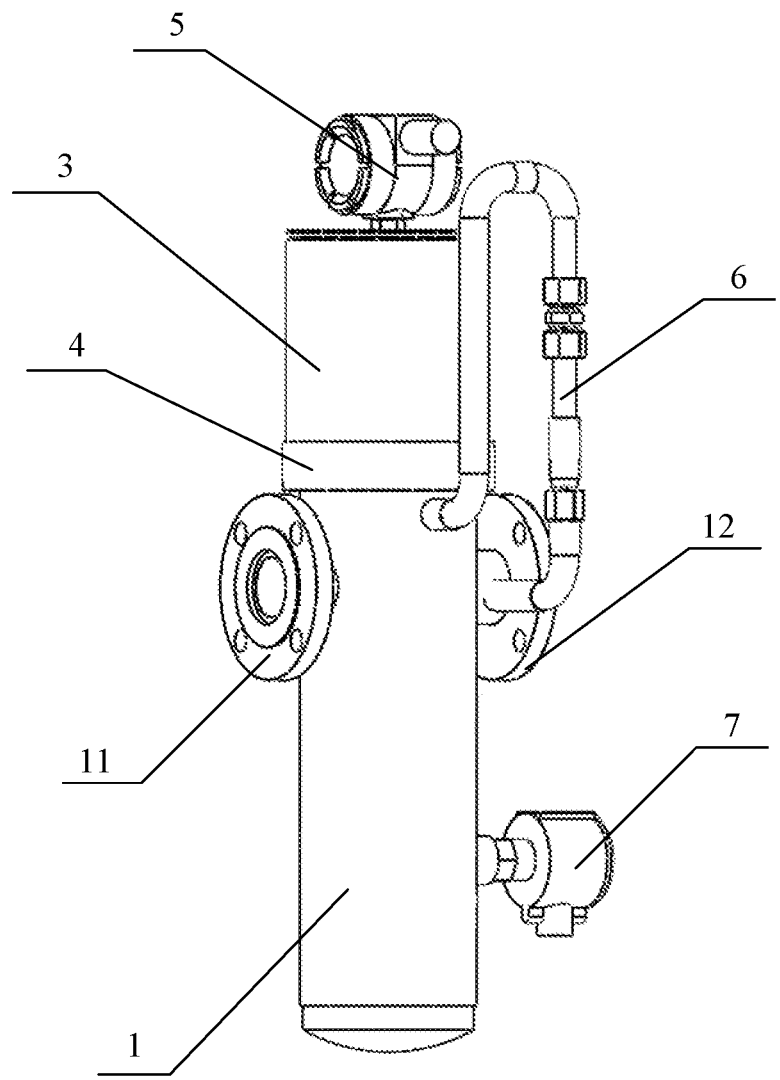
FIG. 1 is a schematic view of an external structure of a crude oil parameter detection device according to an embodiment of the present disclosure.

In order that the objects, technical solutions and advantages of the embodiments of the present disclosure will become clearer, technical solutions in the embodiments of the present disclosure will be described clearly and completely below in conjunction with the drawings in the embodiments of the present disclosure. Apparently, the described embodiments are some of the embodiments of the present disclosure, not all of them. All the other embodiments obtained by those skilled in the art based on the embodiments of the present disclosure without creative efforts will fall within the scope of protection of the present disclosure.

In the following detailed description, reference may be made to various drawings which constitute a part of the present application and which serve to explain specific embodiments of the present application. In the drawings, similar reference signs denote substantially similar components in different figures. The individual specific embodiments of the present application will be described in sufficient detail below to enable those of ordinary knowledge and skills in the art to carry out the technical solutions of the present application. It is understood that other embodiments may be utilized, or structural, logical or electrical changes may be made to the embodiments of the present application.

The present disclosure provides a crude oil parameter detection device, in which a basic detection parameter is a flow rate of an oil transport pipeline connected. A rising height of a float in a measuring tube is determined by detecting a position of a detection part on a float connection rod, thereby calculating a flow rate of measured crude oil. Out of the existing flow metering devices, the float type flowmeter is a widely used device for metering the flow rate of gas and liquid. Metering elements of the float type flowmeter include a measuring tube and an indicator. An interior of the measuring tube is a cone-shaped measuring chamber that gradually expands from bottom to top, with a fluid inlet at a lower end and a fluid outlet at an upper end. A float, which is guided by a guide rod and can move up and down freely, is in-built in the cone-shaped measuring chamber. When the measured fluid flows through the cone-shaped measuring tube from bottom to top, a differential pressure is generated between upper and lower ends of the float to form a rising force. When the rising force acting on the float is greater than the weight of the float immersed in the fluid, the float will rise, and the area of the annular gap between the float and a wall of the measuring tube will increase accordingly; a flow velocity of the fluid at the annular gap decreases immediately, the differential pressure between the upper and lower ends of the float decreases, and the rising force acting on the float also decreases until the rising force equals to the weight of the float immersed in the fluid, at which time the float stabilizes at a certain height, and the area of the annular gap between the float and the wall of the measuring tube remains constant. The area of the annular gap is related to the rising height of the float, that is, a rising position of the float in the measuring tube represents the magnitude of the flow rate. There are usually two types of indicators. One type is to set scales on a tube body, and a value of the scale is determined according to a correspondence between the position and the flow rate. In this type of flowmeter, the flow rate value can be obtained by observing the scale position where the liquid is located. Another type of indicator is a pointer indicator. In this type of flowmeter, the float is in-built with a first steel magnet, the indicator is in-built with a second steel magnet coupled with the first steel magnet, and the second steel magnet is connected to a pointer through a transmission mechanism such as a connection rod. When the float moves up and down and rotates with the measured fluid, a magnetic field generated by the first magnetic steel in-built in the float changes with the movement and rotation of the float. Since the second steel magnet in the indicator is magnetically coupled with the first steel magnet, the second steel magnet rotates with the change of the magnetic field, and the second magnet drives the pointer of the indicator to rotate through the connection rod which serves as the transmission mechanism. After correction, the rising height of the float corresponds to the position of the pointer in a one-to-one correspondence, and the position of the pointer indicates the corresponding flow rate. However, after long-term use of the above-mentioned metal float type flowmeter, due to the limitations of processing and material conditions, the connection rod in the transmission mechanism will not be able to accurately transmit the position of the float due to the fatigue damage suffered, thus resulting in inaccurate measurement and deterioration of the reliability after long-term use. No transmission mechanism is used in the present disclosure, so the present disclosure is not subjected to the fatigue damage of the traditional float position detection assembly, and the accuracy during long-term use can be ensured. In addition, traditional floats have a relatively small weight and cannot adapt to such viscous fluids as crude oil which has a complex composition. In order to adapt to the special flowing state and fluid composition of the crude oil, the device provided by the present disclosure is significantly different from the traditional float type flowmeters in structure. Hereinafter, the present disclosure will be described in detail through specific embodiments as follows.

Figure 2:
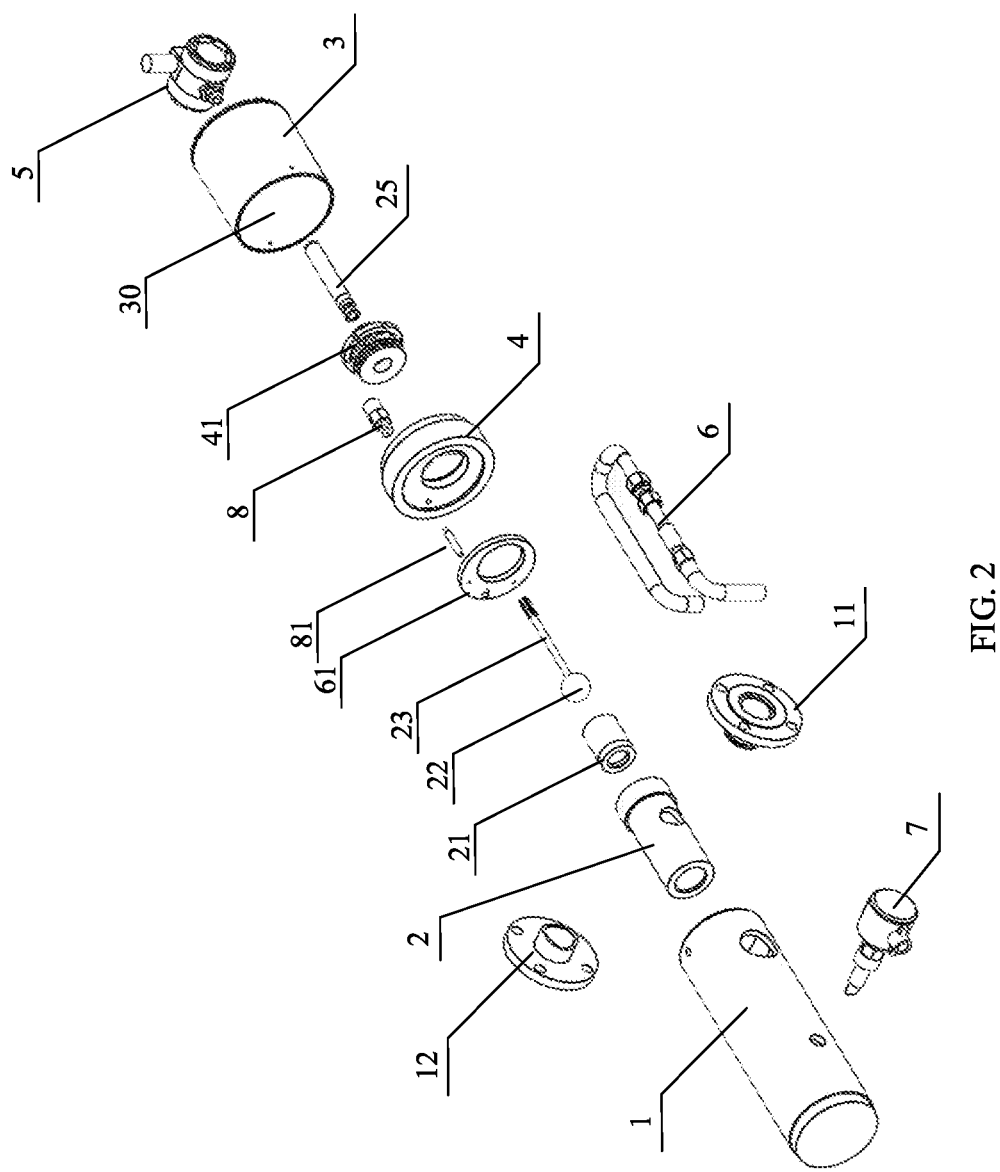
FIG. 2 is an exploded structural view of the crude oil parameter detection device according to the embodiment shown in FIG. 1.
Figure 3:
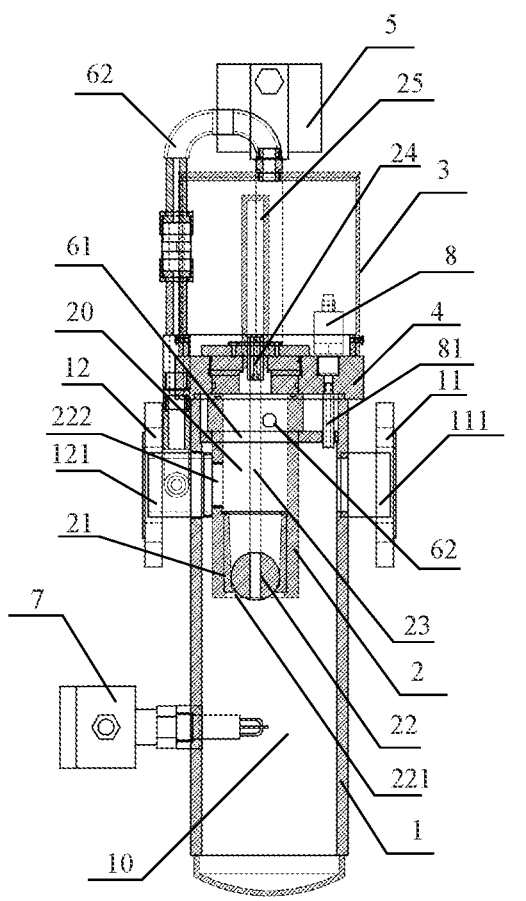
FIGS. 3 to 4 are partial sectional views of the crude oil parameter detection device according to this embodiment of the present disclosure.
Figure 4:
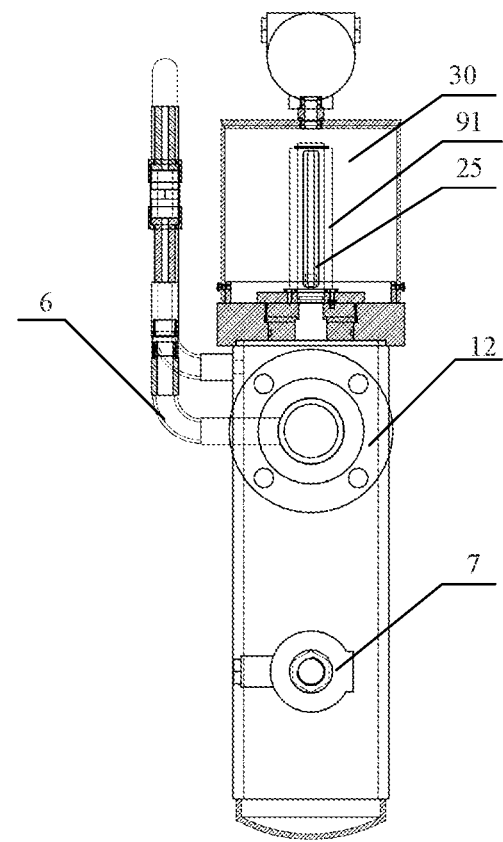

FIG. 1 is a schematic view of an external structure of a crude oil parameter detection device according to an embodiment of the present disclosure, FIG. 2 is an exploded view of the crude oil parameter detection device according to the embodiment shown in FIG. 1, and FIGS. 3 to 4 are partial sectional views of the crude oil parameter detection device according to this embodiment. With reference to FIGS. 1 to 4, the crude oil parameter detection device in this embodiment includes a liquid cavity 10 constituted by a first housing 1. The first housing 1 is provided with a first liquid inlet 111 and a first liquid outlet 121. The first liquid inlet 111 is connected to a liquid inlet connector 11, and the first liquid outlet is connected to a liquid outlet connector 12. The liquid inlet connector 11 and the liquid outlet connector 12 include pipelines and flanges, and the flanges can be connected to the oil transport pipeline. The liquid cavity 10 has a built-in flow measurement cavity 20 constituted by a second housing 2. A second liquid inlet 221 is provided at a bottom of the second housing 2 and a second liquid outlet 222 is provided on a side surface of the second housing 2. A pipeline of the liquid outlet connector 12 extends into the liquid cavity 10 and is connected to the second liquid outlet 222. The crude oil in the oil transport pipeline enters the liquid cavity 10 through the liquid inlet connector 11, then enters the flow measurement cavity 20 through the second liquid inlet 221 at the bottom of the second housing 2, and is then output to the oil transport pipeline through the second liquid outlet 222 and the liquid outlet connector 12.

Figure 5:
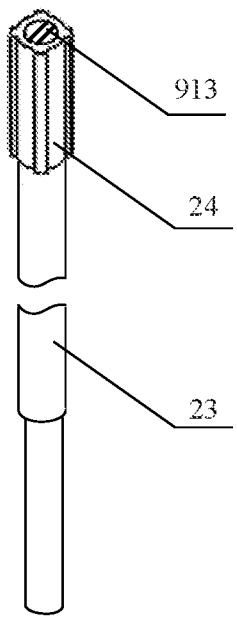
FIG. 5 is a schematic view of a float connection rod according to an embodiment of the present disclosure.

A cone-shaped tube 21 is nested inside the second housing 2, and a cone angle of the cone-shaped tube 21 is not larger than 20 degrees. By changing the cone angle of the cone-shaped tube 21, different flow rates can be adapted to. The cone-shaped tube 21 is in-built with a float assembly, which includes a float 22 and a float connection rod 23 integrally connected with the float 22, and an end of the float connection rod 23 is connected to a detection part. In order to stabilize a movement path of the float in the vertical direction when it moves, a float stabilizing structure 24 is connected to the end of the float connection rod 23 in a better embodiment. As shown in FIG. 5, which is a schematic view of the float connection rod 23, the float stabilizing structure 24 includes a column and a plurality of side edges protruding from a side surface of the column in an axial direction of the column. In this embodiment, there are four side edges in total, and when viewed from the cross section of the column, the four side edges constitute a cross structure. The float in this embodiment is a metal sphere float, which has a diameter larger than the second liquid inlet 221 on the cone-shaped tube 21.

The first housing 1 and the second housing 2 are fixed to a lower part of a connection base 4 which is used as a connector with an upper part thereof being fixed to a third housing 3, and an interior of the third housing 3 constitutes a detection cavity 30. The connection base 4 and an installation base 41 are nested and fixed together. A center of the installation base 41 has a through hole, and is fixedly connected with a connection rod sleeve 25. The connection rod sleeve 25 communicates with the flow measurement cavity 20 via the through hole at the center of the installation base 41. When the float connection rod 23 enters the connection rod sleeve 25, the cross structure at the end of the float rod can make the float connection rod 23 upright so that the float moves in the vertical direction. In addition, the cross structure at the end of the float rod can effectively reduce a contact area between the float connection rod 23 and an inner wall of the connection rod sleeve 25, thereby reducing the friction between the float connection rod 23 and the inner wall of the connection rod sleeve 25 when the float connection rod 23 moves up and down. At the same time, a negative pressure can also be prevented from being generated when there is water and oil in the connection rod sleeve 25, which would otherwise suction the float connection rod 23 and cause the float connection rod 23 to fail to fall back into the measurement cavity normally.

A top of the third housing 3 is connected with a gauge outfit 5. The gauge outfit 5 has a built-in circuit board with circuit elements, and is installed with a display screen and an antenna of a wireless module. The processing module and its peripheral circuits in the device are all arranged on the circuit board in the gauge outfit 5.

A gas separation baffle 61 is arranged between the first housing 1 and the second housing 2, and a plurality of ventilation holes are distributed on the gas separation baffle 61. The first housing 1 is provided with a gas inlet, which is located on the first housing 1 between the gas separation baffle 61 and a lower surface of the connection base 4. A gas outlet is provided on a liquid outlet pipeline of the liquid outlet connector 12, and two ends of a gas pipeline 6 are respectively connected to the gas inlet and the gas outlet through ports. Since the crude oil is a mixed liquid that integrates oil, gas, water, various other liquid components, and solid particles, the gas components in it will more or less affect the metering of the flow rate of the crude oil. In this embodiment, by providing the gas separation baffle 61 on an upper part of the liquid cavity 10, the gas escaping from the crude oil during the flow will penetrate through the gas separation baffle 61, and accumulate above the gas separation baffle 61. The gas pipeline 6 then guides the gas into the liquid outlet pipeline of the device, and the gas flows back to the crude oil transport pipeline along with the liquid, thereby reducing the influence of the gas on the metering of flow rate, and making the metering of flow rate more accurate.

In this embodiment, a hole is provided on the first housing 1 constituting the liquid cavity, and a water content detection device 7 is installed in the hole. A water content sensing end of the water content detection device 7 is in-built in the liquid cavity 10. In an embodiment, the water content detection device 7 has a built-in processor to directly obtain the water content of the liquid in the liquid cavity 10. The water content is sent to the gauge outfit 5, and is stored in a memory, or displayed on the display screen of the gauge outfit 5, or sent to a remote legal device through wireless transmission. In some other embodiments, the water content detection device 7 only senses the liquid in the liquid cavity 10 to obtain water content detection data, and sends it to the processing module of the gauge outfit 5 to calculate the water content of the liquid in the liquid cavity 10.

In this embodiment, a pressure sensor 8 is also connected to the connection base 4, and a pressure sensing part of the pressure sensor 8 is in communication with the liquid cavity 10. A connection pipe 81 passes through the connection base 4 and the gas separation baffle 61, and communicates with the liquid cavity 10, so that the pressure sensor 8 can sense the pressure generated by the crude fluid. A signal end of the pressure sensor 8 is connected to the processing module in the gauge outfit 5, and the processing module calculates a current pipeline pressure according to a pressure sensing signal sent by the pressure sensor 8, or receives pressure value data sent by the pressure sensor 8. The pressure value data is either stored in the memory, or displayed on the display screen, or sent to the remote legal device through wireless transmission.

Reference is made to FIG. 6, which is a block diagram showing the principle of a control device of the crude oil parameter detection device in this embodiment. The control device in this embodiment includes a processing device for metering the flow rate. The processing device includes a data processing module 90, a position detection module 91, a wireless transmission module 92, and a human-computer interaction interface 93. In this embodiment, the water content detection device 7 and the pressure sensor 8 are respectively connected to the data processing module 90 and send their respective data to the data processing module 90. The position detection module 91 is located in the detection cavity 30, and can detect a rising height of the float in the flow measurement cavity 20 and send a height detection signal to the data processing module 90, which calculates the flow rate of the crude oil in the crude oil transport pipeline according to a preset calculation formula. The wireless transmission module 92 is, for example, a wireless module such as Bluetooth, WiFi, or ZigBee, which can transmit the calculated flow data, pressure data, and water content data of the measured fluid to a remote legal device, so that the work staff does not need to read data at the measurement site, while also being capable of receiving parameters and instructions from the remote legal device.

The human-computer interaction interface 93 includes keys and a display screen. The display screen can display various data; for example, regarding an option of the flow rate, it can display an instantaneous flow rate, a cumulative flow rate, and condition parameters used in calculating the flow rate. The display screen can also display relevant data about an option of the pressure and about an option of the water content. The corresponding options can be called by pressing the keys, and the corresponding data will be displayed on the display screen. The corresponding parameters can also be modified through the cooperation of different keys. For example, various parameters used in calculating the flow rate can be input by the work staff with authority through the human-computer interaction interface 93, and the authority can be confirmed by verifying a set password. Of course, it may also be sent to the data processing module 90 through the wireless transmission module 92, and the human-computer interaction interface 93 may of course also be implemented by a touch screen.

FIG. 7 is a schematic structural view of a position detection module according to an embodiment of the present disclosure. In this embodiment, the position detection module 91 is a sensor sleeve, which includes a first sensor sleeve 910 and a plurality of first sensor arrays 911 fixed on an outer surface of a side surface of the first sensor sleeve 910. As shown in the figure, a total of six first sensor arrays 911 are fixed on the outer surface of the side surface of the first sensor sleeve 910, and are arranged in a circumferential direction in a spirally ascending manner. The first sensor sleeve 910 covers the outside of the connection rod sleeve 25, and an end of the first sensor sleeve 910 is fixed together with the connection base 4. Each of the first sensor arrays 911 includes a plurality of Hall sensors 9100 (see FIG. 8) and signal sockets 912 arranged on a chip board, and the chip board is fixed on the first sensor sleeve 910 with the sensors facing inward. The plurality of signal sockets 912 on the chip board are connected in series and connected with the data processing module 90 in the gauge outfit 5.

The end of the float connection rod 23 enters the connection rod sleeve 25 through the connection base 4, and moves therein freely up and down with the measured fluid. A magnet 913 is fixed at the end of the connection rod sleeve 25, as shown in FIG. 5. When the float connection rod 23 moves up and down, the magnet 913 can be sensed by the Hall sensor when it reaches a sensing point of the Hall sensor, thus generating a height detection signal which is then sent to the data processing module 90 in the gauge outfit 5. The magnet 913 in the present disclosure may be a permanent magnet with strong magnetism, such as a neodymium-iron-boron magnet, a samarium-cobalt magnet, an alnico magnet and the like.

Reference is made to FIG. 8, which is a schematic view of the six first sensor arrays 911 in FIG. 7 after being expanded. It can be seen from FIG. 8 that the sensing points of two adjacent Hall sensors in each first sensor array 911 are separated by a distance d=D. Through the other five first sensor arrays 911 arranged in a spirally ascending manner, the sensing distance D in one first sensor array 911 is equally divided into six parts, that is, the sensing distance of two adjacent Hall sensors of the current Hall sensor array is d=D/6. Therefore, the detection accuracy of the sensor arrays in this embodiment is improved by 6 times as compared with only one first sensor array 911. By setting the distance D between two adjacent Hall sensors in one first sensor array 911 and the number of the first sensor arrays 911, sensing distances with different accuracies can be obtained. The accuracy of the sensing distance corresponds to the metering accuracy of the rising height of the float. A distance from the sensing point of the lowermost sensor to the sensing point of the uppermost sensor constitutes the total sensing height $h_T$ of the position detection module 91, which corresponds to the measurement range of flow rate metering of the device, and the corresponding total sensing height $h_T$ may be set according to the actual measurement range in the application scene.

In this embodiment, each sensor has unique position information. For example, a four-digit number is used to represent the position information of a sensor, in which the first two digits represent the numbering of the first sensor array, and the last two digits represent the numbering of the position arranged vertically in the first sensor array. For example, the sensor with position information of 0210 is the $10^{th}$ sensor in the second first sensor array.

Reference is made to FIG. 9, which is a schematic diagram of the calculation principle of the crude oil parameter detection device when the float is a sphere float. It is a partial schematic view of an axial section of the cone-shaped tube. The float moves upward under the action of the measured fluid. When the float is subjected to balanced forces in the measuring tube, it stabilizes at a height, and the height at which the float stops at this time is Δh. The volumetric flow calculation formula 1-1 of the crude oil parameter detection device is:

$$q_v = \alpha \varepsilon \Delta F \sqrt{\frac{2gV_f(\rho_f - \rho)}{\rho F_f}}; \qquad 1\text{-}1$$

where $q_v$ is a volumetric flow, $\alpha$ is a flow coefficient of the device, $\varepsilon$ is a gas expansion coefficient when the measured fluid is a gas (the present disclosure is used for crude oil metering, and the crude oil is an incompressible fluid, of which $\varepsilon$=1), g is the acceleration of gravity, $V_f$ is a volume of the float or the sphere float, $\rho f$ is a density of the material of the float, $\rho$ is a density of the measured fluid, $F_f$ is a cross-sectional area of the float at the maximum working position, $\Delta F$ is a circulation annular area, $\theta$ is a cone angle of the measuring tube, and $\Delta h$ is a height of the float from its lowest point to a current measurement position.

When the float is a sphere, $R_f$ is a radius of the sphere float; Rp is a corresponding working radius of the measuring tube at the position where the float is located:

where $Rp=(R_f+\Delta h \sin(\theta/2))$ \hfill 1-2

$\Delta F=\pi Rp^2 - F_f$ \hfill 1-3

$F_f = \pi R_f^2$ \hfill 1-4.

By substituting the above three formulas into formula 1-1, the following formula 1-5 is obtained:

$q_v = \alpha[\pi(R_f+\Delta h \sin(\theta/2))^2 - \pi R_f^2]\sqrt{2gV_f(\rho_f-\rho)/\rho\pi R_f^2}$ \hfill 1-5.

In formula 1-5, except for the height Δh of the float from its lowest point to the current measurement position, all other parameters are known parameters. When the value of the rising height Δh of the float is obtained, the instantaneous flow rate of the measured crude oil fluid can be calculated through formula 1-5, and a cumulative flow rate for a period of time can be obtained through the following formula 1-6:

$Q_t = Q_0 + \int_0^t q_t dt$ \hfill 1-6;

where $Q_t$ represents the cumulative flow rate at time t, $Q_0$ represents the cumulative flow rate at time t=0, $q_t$ represents the instantaneous flow rate at time t, and t represents time (the unit being s).

In addition to the spherical shape, the float in the present disclosure may also be any structural body which has a circular working cross section and which is symmetrical with respect to a vertical centerline, such as a cylinder, a cone, an ellipsoid, a sphere, etc.; or the float may be any structural body obtained after a combination of the above various shapes so that the float can be subjected to uniform forces in all directions and can move up and down stably in the measured crude oil. In this embodiment, the float is the sphere shown in FIG. 1, and the contact between the sphere float and the inner wall of the cone-shaped tube 21 is line contact. As compared with other shapes, firstly, the friction generated when the sphere float is in contact with the inner wall of the measuring tube can be ignored, thus simplifying the force application condition on the sphere float and making the calculation process more accurate so that the accuracy of the measurement is improved; secondly, when the measured fluid is a liquid having a certain viscosity, such as the crude oil, the curved surface of the float is advantageous for reducing the impedance of the viscous liquid to the up-and-down movement of the float in the liquid.

As shown in FIG. 10, a schematic diagram of the calculation principle of the crude oil parameter detection device when the float is a gyroscopic float is illustrated. In a case where the float is gyroscopic, when it is impacted by a large flow of fluid, its own rotation reduces the swinging in the lateral direction, so that it can move up and down stably in the vertical direction. FIG. 10 is a partial schematic view of an axial section of the cone-shaped tube. The volumetric flow calculation formula 1-1 of the crude oil parameter detection device is:

$$q_v = \alpha \varepsilon \Delta F \sqrt{\frac{2gV_f(\rho_f - \rho)}{\rho F_f}}; \qquad 1\text{-}1$$

where $q_v$ is a volumetric flow, $\alpha$ is a flow coefficient of the flowmeter, $\varepsilon$ is a gas expansion coefficient when the measured fluid is a gas (the present disclosure is used for crude oil metering, and the crude oil is an incompressible fluid, of which $\varepsilon$=1), g is the acceleration of gravity, $V_f$ is a volume of the float, $\rho_f$ is a density of the material of the float, p is a density of the measured fluid, $F_f$ is a maximum cross-sectional area of the float, $\Delta F$ is a circulation annular area, $\theta$ is a cone angle of the measuring tube, Δh is a height of the float from its lowest point to a current measurement position, Rp is a corresponding working radius of the measuring tube at the position where the float is located, and $R_f$ is a working radius of the float;

where $Rp=(Rf+\Delta h \tan(\theta/2))$ \hfill 1-7

$\Delta F=\pi Rp^2 - F_f$ \hfill 1-3

$F_f = \pi R_f^2$ \hfill 1-4.

By substituting the above three formulas into formula 1-1, the following formula 1-8 is obtained:

$q_v = \alpha[\pi(Rf+\Delta h \tan(\theta/2))^2 - \pi R_f^2]\sqrt{2gV_f(\rho_f-\rho)/\rho\pi R_f^2}$ \hfill 1-8.

In formula 1-8, except for the height Δh of the float from its lowest point to the current measurement position, all other parameters are known parameters. When the value of the rising height Δh of the float is obtained, the instantaneous flow rate of the measured fluid can be calculated through formula 1-8, and a cumulative flow rate for a period of time can be obtained through the above formula 1-6.

When the data processing module 90 receives the signal sent by the sensor array, it can determine the position of the sensor according to the position information, and then query an internal table of the correspondence between the sensor and the height, so that the height value can be obtained, which corresponds to the rising height value Δh of the float in the measurement cavity. When a sphere float is used as the float in the current device, the data processing module 90 uses formula 1-5 to calculate the instantaneous flow rate. When a gyroscopic float is used as the float in the current device, the data processing module 90 uses formula 1-8 to calculate the instantaneous flow rate and uses formula 1-6 to calculate the cumulative flow rate, so that the flow rate data of the measured petroleum transport pipeline can be obtained.

Figure 12:
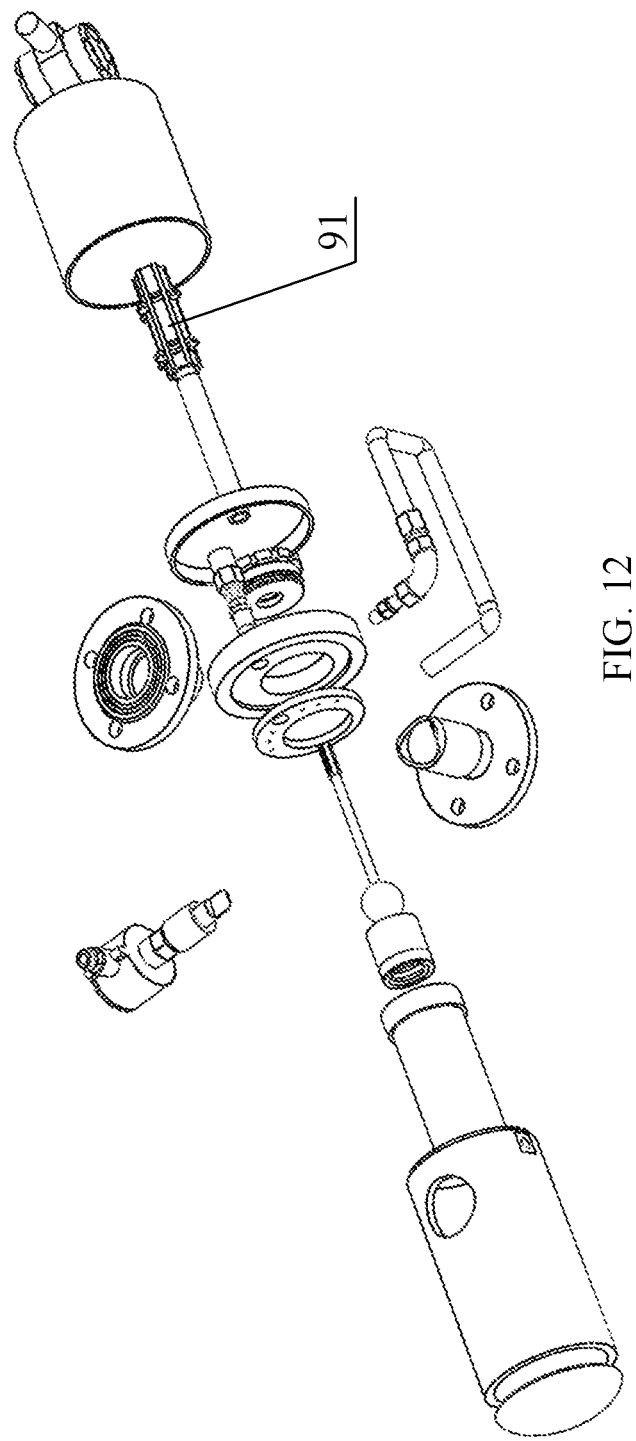
FIG. 12 is a schematic exploded structural view of the crude oil parameter detection device shown in FIG. 11.

FIG. 11 is a schematic view of an external appearance of another crude oil parameter detection device, which has a similar structure to the embodiment shown in FIG. 1, except that the liquid cavity in FIG. 11 is smaller. FIG. 12 shows an exploded view of the crude oil parameter detection device shown in FIG. 11. It can be seen that the position detection module 91 is a sensor sleeve, which is the same as that in FIG. 1, so a repeated description is omitted herein.

The connector used to connect the detection cavity 30, the liquid cavity 10 and the flow measurement cavity 20 in the foregoing embodiment is the connection base 4 and the installation base 41 inside it. In another connection mode, the flange connection shown in FIG. 13 may also be used. The connector includes an upper flange 43 and a lower flange 44. The first housing 1 is connected to a lower part of the lower flange 44, and the second housing 2 is fixed to a lower part of the lower flange 44 through the installation base. Through holes are provided at the centers of the upper flange 43 and the lower flange 44 to allow the float connection rod 23 to pass through. The third housing 3 is connected to an upper part of the upper flange 43, and a sensor sleeve serving as the position detection module 91 is fixed on the upper flange 43.

Figure 13:
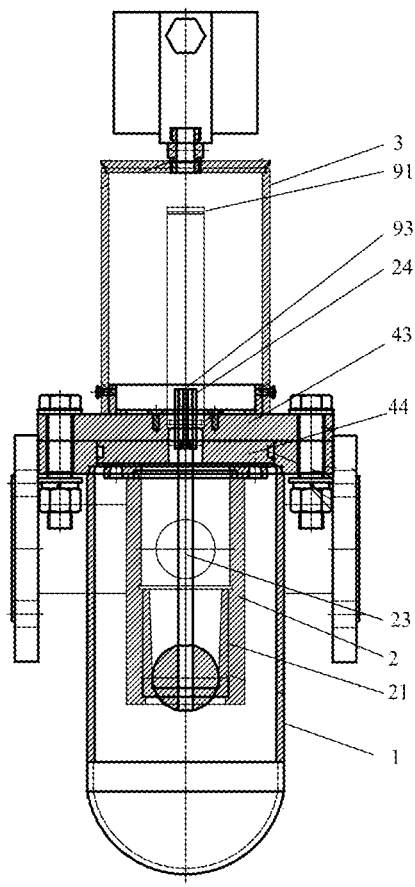
FIG. 13 is a partial sectional view of a crude oil parameter detection device according to an embodiment of the present disclosure.

In the embodiment shown in FIG. 13, when compared with the structure of the device shown in FIG. 11, the gas separation structure, the water content detection device and the pressure sensor are not provided in this embodiment. Therefore, the processing module in the gauge outfit in this embodiment only needs to calculate the flow rate data, and display or transmit the flow rate data to a remote end. Of course, according to application requirements, a water content detection device and a pressure sensor may be added to the structure shown in FIG. 13. In addition, regarding the gas separation structure, due to the different components of the crude oil produced by different oil wells, more gas will affect the accuracy of metering the flow rate, so gas separation is required before metering the flow rate. At this time, a device with a gas separation structure as shown in FIGS. 1 and 11 may be used, or other gas separation devices may also be separately provided in the transport pipeline. The structure shown in FIG. 13 is connected to the transport pipeline having a gas separation device added thereon. Since the gas separation has been performed when the liquid flows through the device, the device does not need to be provided with a gas separation structure. In addition, the petroleum produced from some oil wells does not contain much gas, and gas separation is not required in this case, so the device shown in FIG. 13 can be connected to the transport pipeline to meter the flow rate.

The position detection module in each of the foregoing embodiments is a Hall sensor array; of course, other sensors or position detection methods may also be used. For example, the present disclosure can also detect the rising position of the float through an image capture device or a photoelectric sensor arranged in the detection cavity when in cooperation with a dividing ruler.

Figure 14A:
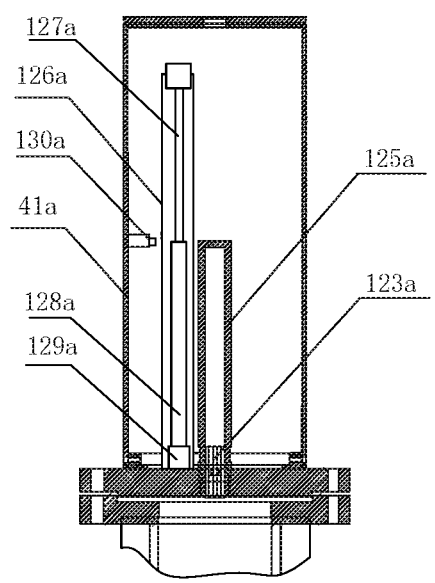
FIGS. 14A to 14C are schematic partial sectional views of a crude oil parameter detection device according to another three embodiments of the present disclosure.

As shown in FIG. 14A, a bracket 126a is provided outside of the connection rod sleeve 125a, and a slideway 127a is provided in the bracket 126a. A moving block 129a is provided at a position corresponding to the magnet 123a, and the moving block 129a is connected to a dividing ruler 128a. In an embodiment, the moving block 129a is an iron block. When the float rises in the measuring tube, the magnet 123a at its end rises and attracts the moving block 129a to rise together, and the dividing ruler 128a connected to the moving block 129a rises at the same time. Corresponding to the end of the connection rod sleeve 125a, an image capture device 130a, such as a camera, is installed on the housing 41a. Scales of the dividing ruler 128a are marked from top to bottom; that is, when the float is at the bottom, the top position of the dividing ruler 128a corresponding to the image capture device 130a is a starting position 0, and starting from 0 and going downward, the position of the moving block 129a is the maximum scale. When the float rises, the magnet 123a at its end attracts the moving block 129a to drive the dividing ruler 128a to rise, and the image capture device 130a collects the current image of the dividing ruler, so that the rising height of the float can be obtained through the image recognition of the processing module.

Figure 14B:
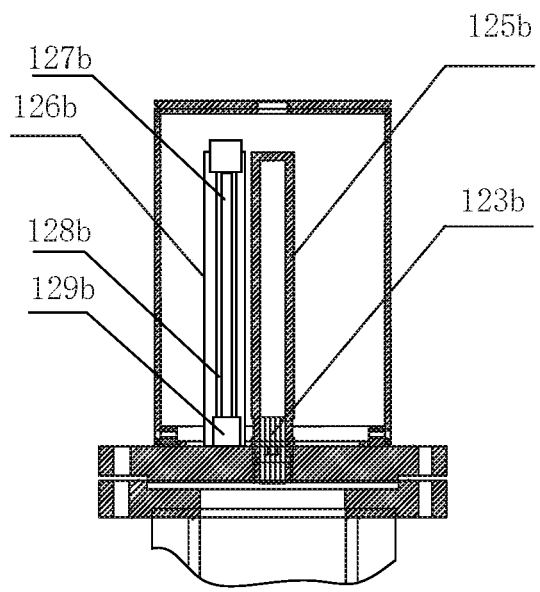

As shown in FIG. 14B, in this embodiment, a dividing ruler 128b is fixed to a bracket 126b, and the starting position of the dividing ruler 128b is at the lowermost moving block 129b. Moreover, its scales are represented by the depth. A photoelectric sensor is provided on the moving block 129b. When the moving block 129b rises with the magnet 123a along a slideway 127b, light emitted from a light emitter of the photoelectric sensor is irradiated onto the dividing ruler 128b, and a light receiver receives the light reflected back from the dividing ruler 128b, so that the current scale of the dividing ruler 128b is determined according to the change in the light energy of the received light signal.

In addition, other methods can also be used to realize the tracking movement of the moving blocks and magnets 123a and 123b. For example, Hall sensors and linear motors are provided on the moving blocks 129a and 129b. When the hall sensors sense the magnets 123a and 123b, the linear motors drive the dividing ruler 128a or the photoelectric sensor to follow the magnets 123a and 123b to move.

Figure 14C:
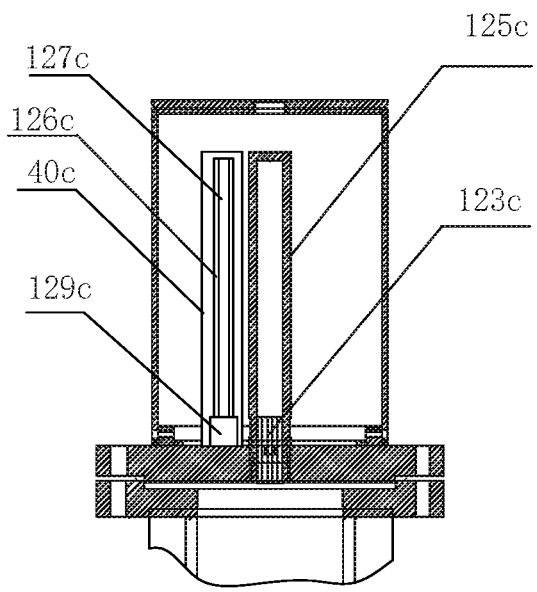
Figure 15A:
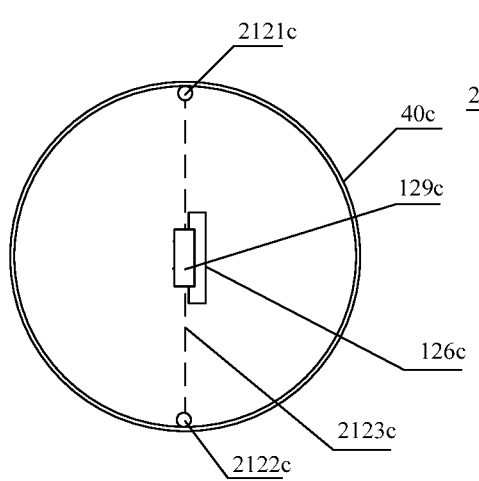
FIGS. 15A to 15B are schematic views of the arrangement of photoelectric sensors according to two embodiments of the present disclosure.

As shown in FIG. 14C, in this embodiment, a sensor sleeve 40c is provided, which is sleeved outside a bracket 126c, a slideway 127c and a moving block 129c. In some other embodiments, there is no need to provide a dividing ruler, but a plurality of photoelectric sensors are provided on the sensor sleeve 40c to form a sensor array. The section of the sensor sleeve 40c is shown in FIG. 15A. The sensor array is composed of a plurality of photoelectric sensors 212c vertically arranged on an inner surface of a side surface of the sensor sleeve 40c. Each photoelectric sensor 212c at a horizontal position includes a light emitting part 2121c and a light receiving part 2122c, both of which are fixed on the sensor sleeve 40c. A path 2123c formed by the light emitting part 2121c and the light receiving part 2122c intersects the up-and-down vertical movement path of the moving block 129c. The float connection rod moves telescopically in the second sensor sleeve 125c, and drives the moving block 129c in the sensor sleeve 40c to move on the slideway 127c. When it blocks the path 2123c formed by the light emitting part 2121c and the light receiving part 2122c of one photoelectric sensor, the photoelectric sensor sends a signal. The position of the float connection rod can be determined according to the position of the photoelectric sensor that sends the signal, so that the rising height of the float when it rises from the lowest point to the detection position can be obtained.

Figure 15B:
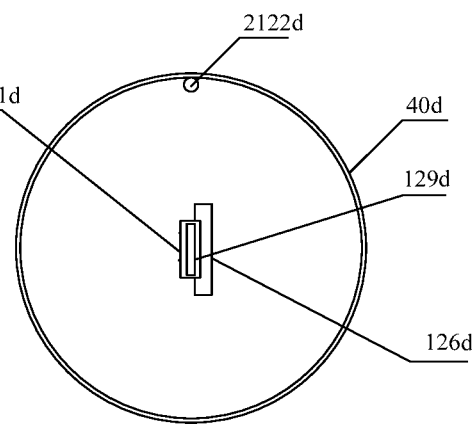

In another embodiment, as shown in FIG. 15B, the sensor array on a sensor sleeve 40d is composed of light receiving parts 2122d of a plurality of photoelectric sensors, the light receiving parts 2122d are installed on an inner wall of the sensor sleeve 40d, and light emitting parts 2121d are installed on a moving block 129d. The light emitting parts 2121d always emit light. When the moving block 129d moves on a slideway 127d, the light emitted from the light emitting parts 2121d can be received by the light receiving parts 2122d at different heights, and electrical signals can be sent. The position of the float connection rod can be determined by the processing module according to the position of the photoelectric sensor that sends the electrical signal.

The processing module stores the table of correspondence between the sensor position and the height, and the processing module queries the table of correspondence according to the sensor position to obtain the rising height of the float, so that the flow rate of the measured petroleum can be calculated. For the specific process, reference may be made to the embodiment in which the Hall sensors are used as the sensor array, for which a detailed description will be omitted herein.

The above position detection module and the corresponding structure only reveal the relevant position detection means. Those skilled in the art can choose any of the above detection means as actually required, or obtain the relevant position detection structure under the teaching of the above detection means.

In summary, the detection device provided by the present disclosure can be directly connected to the crude oil transport pipeline, has a small volume, occupies a small space, is convenient for installation and daily maintenance. This device can measure the flow rate in the crude oil transport pipeline. Since the transmission device in the traditional float flowmeters is not required, the measurement accuracy will not be affected by the fatigue damage caused by the transmission device in the long-term use. Moreover, the present disclosure can be integrated with other parameter detection devices in view of actual application requirements, so that multiple types of data can be detected. The device has a strong and durable structure, can be applied to various field environments and work stably for a long time.

The above embodiments are only for the purpose of illustrating the present disclosure, rather than limiting the present disclosure. Those skilled in the relevant technical field may make various changes and modifications without departing from the scope of the present disclosure. Therefore, all the equivalent technical solutions should also fall within the scope of the present disclosure.

What is claimed is:

1. A crude oil parameter detection device, comprising:
   a liquid cavity, which is constituted by a first housing and comprises a first liquid inlet and a first liquid outlet;
   a flow measurement cavity, which is constituted by a second housing and in-built in the liquid cavity, and comprises a second liquid inlet and a second liquid outlet, the second liquid outlet being in communication with the first liquid outlet through a liquid outlet pipeline;
   a float assembly, which is in-built in the flow measurement cavity, and comprises a float and a float connection rod integrally connected with the float, an end of the float connection rod being connected to a detection part;
   a detection cavity, which is constituted by a third housing, and at least internally comprises a position detection module;
   a connector, an upper part of which is fixed to the third housing constituting the detection cavity, and a lower part of which is connected to the first housing constituting the liquid cavity and the second housing constituting the flow measurement cavity respectively, in which the connector is provided with a through hole, and the end of the float connection rod can extend into the detection cavity via the through hole; and
   a processing module, which is configured to be at least connected to the position detection module, in which when the detection part at the end of the float connection rod extends into the detection cavity, the position detection module detects a position of the detection part at the end of the float connection rod to obtain a float height detection signal; and the processing module calculates a flow rate of measured crude oil according to the float height detection signal.

2. The crude oil parameter detection device according to claim 1, wherein the first liquid inlet and the first liquid outlet are respectively connected with pipeline connectors for connecting with a crude oil transport pipeline.

3. The crude oil parameter detection device according to claim 1, wherein centers of the first liquid inlet and the first liquid outlet are located on the same cross section of the liquid cavity.

4. The crude oil parameter detection device according to claim 1, wherein the second liquid inlet is provided at a bottom of the flow measurement cavity, and the second liquid outlet is provided on a side surface of the flow measurement cavity.

5. The crude oil parameter detection device according to claim 1, wherein the float is a structural body which has a circular working cross section and which is symmetrical with respect to a vertical centerline.

6. The crude oil parameter detection device according to claim 1, further comprising:
   a connection rod sleeve, which is arranged in the detection cavity, fixed to the upper part of the connector, and is in communication with the through hole in the connector; and
   a float stabilizing structure, which is connected to the end of the float connection rod, and which comprises a column and a plurality of side edges protruding from a side surface of the column in an axial direction of the column;
   wherein when the float rises, the end of the float connection rod and the float stabilizing structure extend into the connection rod sleeve.

7. The crude oil parameter detection device according to claim 1, further comprising:
   a gas separation baffle, which is in-built in the liquid cavity and placed between the second housing and the first housing with a plurality of ventilation holes distributed thereon;
   a gas inlet, which is provided on the first housing between the gas separation baffle and a lower surface of the connector;
   a gas outlet, which is provided on the liquid outlet pipeline located outside the liquid cavity; and
   a gas pipeline, two ends of which are connected to the gas inlet and the gas outlet through interfaces respectively.

8. The crude oil parameter detection device according to claim 1, further comprising a pressure sensor which is configured to be installed on the upper part of the connector;
   wherein a pressure sensing part of the pressure sensor communicates into the liquid cavity through the connector, and a signal end of the pressure sensor is connected to the processing module; and
   wherein the processing module calculates a current pipeline pressure according to a pressure sensing signal sent by the pressure sensor, or receives pressure value data sent by the pressure sensor.

9. The crude oil parameter detection device according to claim 1, further comprising a water content detection device; wherein a connection base of the water content detection device is installed in the first housing constituting the liquid cavity, a water content sensing end of the water content detection device is in-built in the liquid cavity, and a signal end of the water content detection device is connected to the processing module; and
wherein the processing module calculates a current water content according to a water content sensing signal sent by the water content detection device, or receives water content data sent by the water content detection device.

10. The crude oil parameter detection device according to claim 1, wherein the position detection module is a sensor array, and when the detection part at the end of the float connection rod moves vertically up and down in the detection cavity, sensors in the sensor array output the float height detection signal when they detect the detection part.

11. The crude oil parameter detection device according to claim 10, wherein the sensor array is composed of a plurality of Hall sensors, which are arranged into a first sensor array in an up-and-down vertical movement direction of the float connection rod; a plurality of first sensor arrays are arranged on an outer surface of a side surface of a first sensor sleeve in a spirally ascending manner in an up-and-down vertical movement direction of the float connection rod; and the detection part at the end of the float connection rod is a magnet.

12. The crude oil parameter detection device according to claim 10, wherein the sensor array is composed of a plurality of photoelectric sensors arranged on an inner surface of a side surface of a second sensor sleeve.

13. The crude oil parameter detection device according to claim 10, wherein a detection signal output by the sensor array comprises position information and data information, and the position information comprises the position of the sensor that sends the data information in the sensor array.

14. The crude oil parameter detection device according to claim 1, wherein the position detection module comprises an image capture device or a photoelectric sensor arranged in the detection cavity, and a dividing ruler.

15. The crude oil parameter detection device according to claim 1, wherein a gauge outfit which communicates with the third housing is installed on the third housing, and the processing module is located inside the gauge outfit.

16. The crude oil parameter detection device according to claim 15, wherein the gauge outfit comprises:
a human-computer interaction interface, which is connected to the processing module and is configured to display data and input data; and/or
a wireless transmission module, which is connected to the processing module and is configured to send obtained detection data to a remote legal device, and/or receive data from the remote legal device.

* * * * *